(12) United States Patent
Cohen et al.

(10) Patent No.: US 6,350,235 B1
(45) Date of Patent: Feb. 26, 2002

(54) TONGUE DEPRESSOR AND THROAT VIEWING ASSEMBLY

(76) Inventors: Gerard Cohen, Bareket 3, Givat Haslaim, P.O. Box 03839, Rosh Haain; Alexander Strovinsky, 24 Kaplinsky St., Rishon Lezion 75241, both of (IL)

( * ) Notice: Subject to any disclaimer, the term of this patent is extended or adjusted under 35 U.S.C. 154(b) by 0 days.

(21) Appl. No.: 09/684,325

(22) Filed: Oct. 10, 2000

(30) Foreign Application Priority Data

Sep. 13, 2000 (IL) ................................................ 138441

(51) Int. Cl.⁷ ............................................... A61B 1/267
(52) U.S. Cl. ....................... 600/199; 600/240; 600/241; 600/185
(58) Field of Search ................................ 600/185, 188, 600/190, 199, 240, 241, 245, 235, 549, 586

(56) References Cited

U.S. PATENT DOCUMENTS

| | | | |
|---|---|---|---|
| 4,314,551 A | | 2/1982 | Kadell |
| 4,947,829 A | * | 8/1990 | Bullard |
| 5,249,585 A | * | 10/1993 | Turner et al. .................. 607/99 |
| 5,827,178 A | * | 10/1998 | Berall .......................... 600/185 |
| 5,951,461 A | * | 9/1999 | Nyo et al. .................... 600/118 |
| 6,050,938 A | * | 4/2000 | Creed et al. ................. 600/101 |
| 6,123,666 A | * | 9/2000 | Wrenn et al. ................ 600/188 |

* cited by examiner

*Primary Examiner*—Jeffrey A. Smith
(74) *Attorney, Agent, or Firm*—Browdy and Neimark

(57) ABSTRACT

A tongue depressor and throat viewing assembly which includes a disposable flat blade for depressing the tongue of a subject in order to expose his larynx for inspection so that its condition can be diagnosed. Attachable to the trailing end of the blade is a light source and throat viewer unit which projects a light beam to illuminate the exposed larynx and to obtain a digital image thereof which is conveyed to an external computer monitor station. At this station, the image is exhibited on a screen, and is stored in a database for future use.

16 Claims, 3 Drawing Sheets

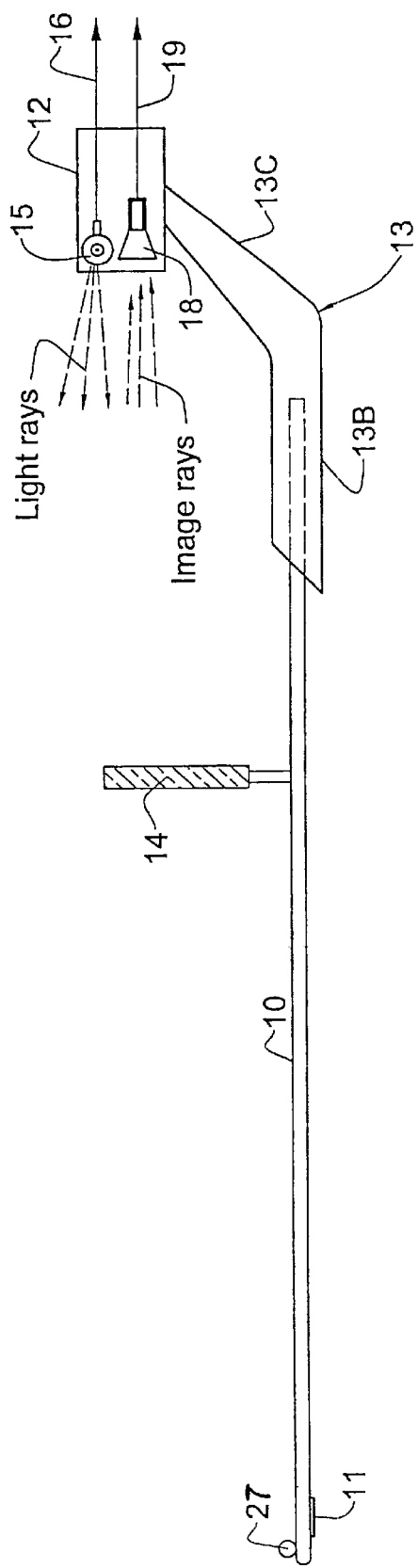
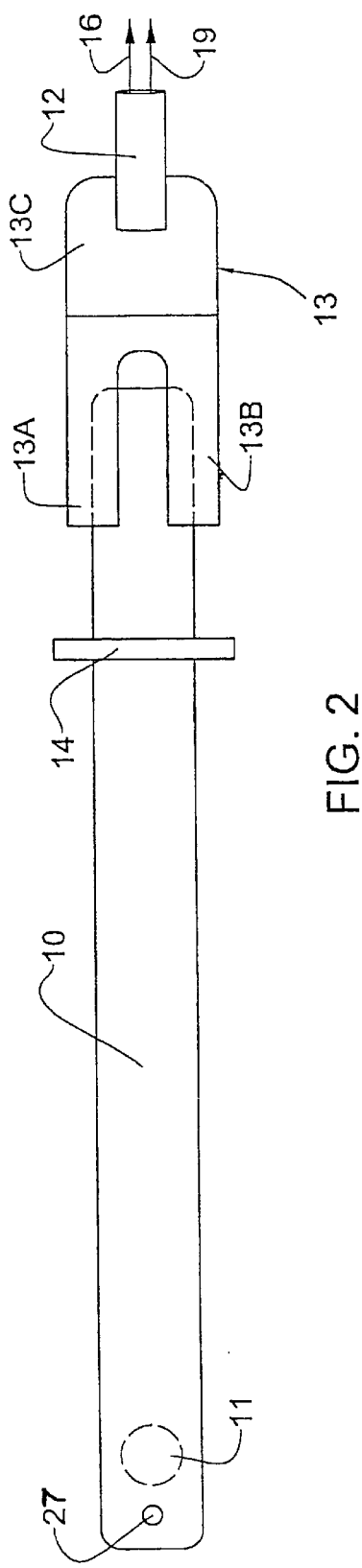
FIG. 1
FIG. 2

TONGUE DEPRESSOR AND THROAT VIEWING ASSEMBLY

FIELD OF THE INVENTION

This invention relates generally to medical appliances to facilitate an inspection of the larynx and a diagnosis of its condition, and more particularly to a tongue depressor and throat viewing assembly for this purpose.

STATUS OF PRIOR ART AND BACKGROUND OF THE INVENTION

The larynx is a cartilagenous organ in the throat containing the vocal chords. It is shaped generally like a tube that is wide at the top and narrower at its lower portion where the larynx joins the trachea. Associated with the larynx is the epiglottis, a valve-like structure at the base of the tongue. The epiglottis is a leaf-shaped member formed of elastic cartilage that projects backward over the tongue during swallowing. It acts like a lid to prevent food from invading this organ. In order therefore to be able to view and examine the larynx, the epiglottis must be lifted.

Inasmuch as an assembly in accordance with the invention includes a blade for depressing the tongue to expose the larynx and a light source associated with the blade to illuminate the exposed larynx, of prior art interest is a laryngoscope, such. as the instrument disclosed in U.S. Pat. No. 4,314,551 to Kadell.

The function of a laryngoscope is to expose the larynx of an anaesthetized patient in order to be able to inject a tube into the trachea a procedure known as a endotrachael incubation. In the Kadell laryngoscope, extending from a handgrip is a blade for depressing the tongue, a light bulb being mounted on the blade to project a beam of light toward its forward end. This bulb is powered by a battery contained in the hand grip.

A larynx is subject to various disorders, among which is laryngitis, an inflammation of the larynx often occurring as a complication of other inflammatory diseases of the upper respiratory system. Diphtheria is a disease marked by the formation of a false membrane in the throat which can cause severe respiratory difficulties, Benign tumors in the larynx are not uncommon, nor are the more serious cancers of the larynx.

In order for a physician to be able to diagnose a larynx disorder, he must be able to clearly view its inflammatory state as well as the presence of polyps, ulcers and nodules or whatever other abnormal conditions are symptomatic of the disease suffered by the patient.

A doctor, by means of a tongue depressor, can expose the larynx and then illuminate the exposed larynx so that it can be inspected and its condition diagnosed. The difficulty experienced with standard clinical procedures for larynx examination is that to conduct this examination, one must first induce in the patient a gag reflex causing the throat to dilate to fully expose the larynx to view. But this exposure period is very brief and does not allow an examining physician sufficient time to adequately inspect the larynx.

Thus many larynx infections result in the production of pus, a whitish fluid formed by suppuration and composed of exudate that includes white blood cells and tissue debris. The presence of whitish pus on the surface of the larynx may be indicative of a serious infection, yet in the brief gag reflex period during which the larynx is exposed to view, the pus may escape the attention of the examining physician and therefore result in an incorrect diagnosis.

While some abnormalities deform the structure of the larynx, these deformations may not show up in the brief period of larynx exposure. Because a doctor cannot in a single gag reflex period induced in a patient make an adequate inspection of the larynx, in many cases he will subject his patient to a succession of gag reflexes, in each one of which, the patient seeks to vomit. This is an ordeal that is hard for a patient to tolerate even more so when the patient is a child who may refuse to undergo this experience. Yet the ability of a physician to make a proper larynx examination is hampered when the physician is unable to do more than just glance at the larynx.

Moreover, in modem medicine, a physician is called upon to go well beyond a diagnosis of a disorder and a prescribed treatment therefor. It is important that the physician make a detailed account of his examination, diagnosis and pre-scribed treatment, for this record makes it possible to evaluate the effectiveness of the treatment. By making a record of the initial examination and diagnosis of the patient's condition, the record can later be compared with records subsequently made in the course of treatment. This comparison indicates the progress made by the patient, or the lack of progress. When it becomes advisable for a patient to consult a specialist in regard to his condition, records made of prior examination and treatment can then be made available to the specialist.

Records regarding a particular patient undergoing treatment are best stored digitally in the database or memory of a computer, for then these records are transmittable via an Internet highway to web sites and E-mail addresses of health care organizations, physicians and others who need to be informed of the patient's condition and treatment. Present methods for maintaining records regarding patients suffering from larynx disorders do not readily lend themselves to computer processing nor to Internet transmission.

SUMMARY OF THE INVENTION

In view of the foregoing, the main object of this invention is to provide a tongue depressor and throat viewing assembly which makes it possible to fully expose and illuminate the larynx of a subject and to obtain a digital image thereof that can be exhibited stored and transmitted.

More particularly, an object of his invention is to provide an assembly of the above type in which the digital image signal yielded by the assembly is conveyed to a computer monitor station at which the image is exhibited on a screen, and is there recorded and stored to produce a record that can be transmitted by Internet to other sites, or otherwise made available to doctors.

A significant advantage of an assembly in accordance with the invention is that it makes it possible to obtain an image of the larynx and to record the image produced when the larynx is fully exposed as a result of a gag reflex induced by the tongue depressor, the assembly taking, as it were, a single picture which is an enlarged view of the larynx revealing all aspects of its condition. This picture can be studied by the doctor for as long as it is necessary to make a proper diagnosis.

Also an object of the invention is to provide an assembly constituted by a disposable, low cost blade and a light source and viewer unit attachable to the blade, the unit being formed of commercially-available components that are relatively inexpensive.

Briefly stated, these objects are attained in a tongue depressor and throat viewing assembly which includes a disposable flat blade for depressing the tongue of a subject in order to expose his larynx for inspection so that its condition can be diagnosed. Adhered to the blade adjacent its leading end is a temperature-sensitive chromatic sticker which assumes a color indicative of the temperature in the region of the larynx.

Attachable to the trailing end of the blade is a light source and throat viewer unit which projects a light beam to illuminate the exposed larynx and which obtains a digital image thereof and of the sticker, these being conveyed to an external display or to a computer monitor station. At this station, the image is exhibited on a screen, and is stored in a database for future use.

BRIEF DESCRIPTION OF THE DRAWINGS

For a better understanding of the invention as well as other objects and features thereof, reference is made to the annexed drawings wherein:

FIG. 1 is a side view of a tongue depressor and throat viewing assembly in accordance with one embodiment of the invention;

FIG. 2 is a top view of the assembly;

DETAILED DESCRIPTION OF THE INVENTION

Figure 3:
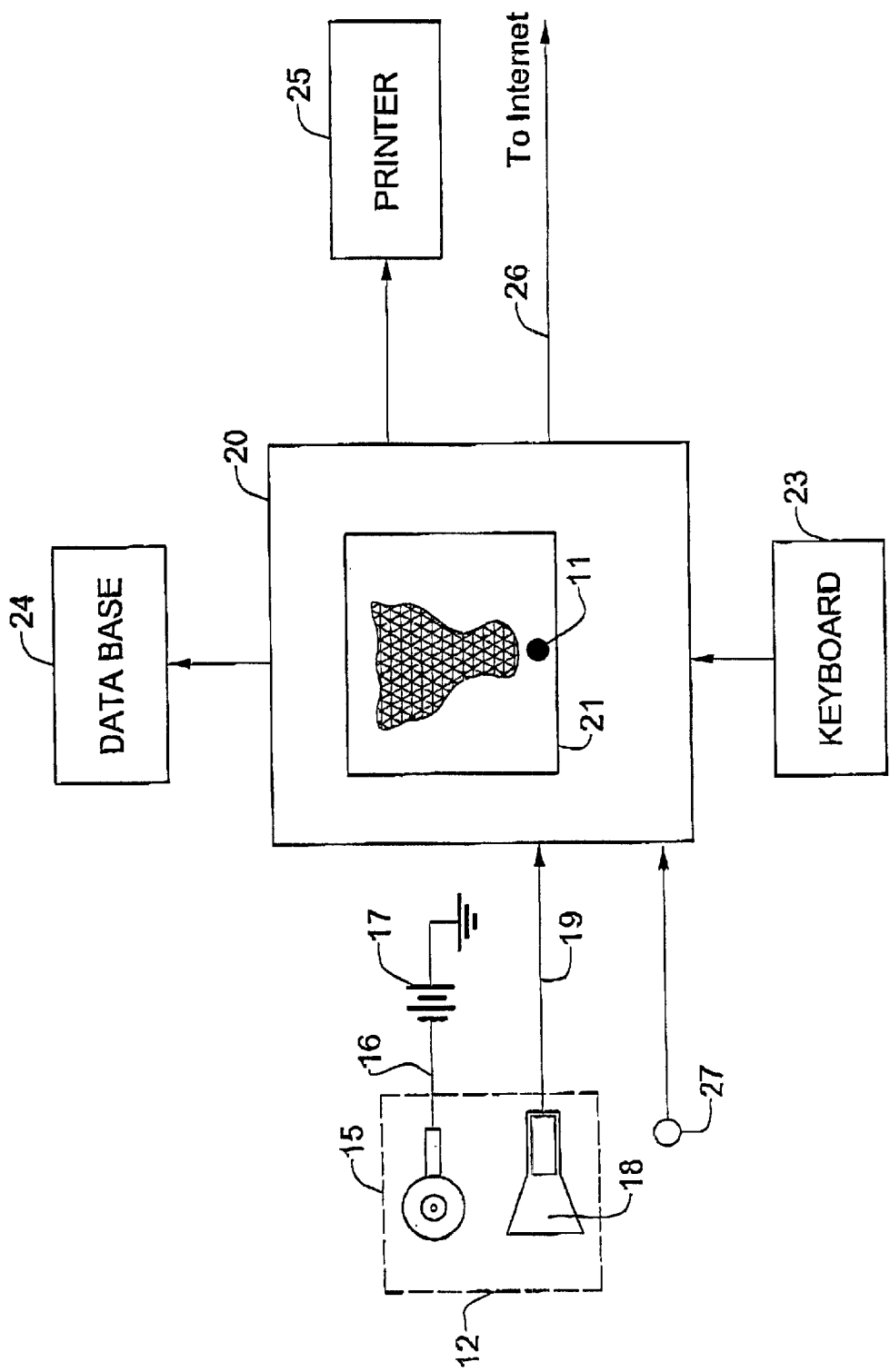
FIG. 3 is a block diagram of the computer monitor station associated with the assembly.

First Embodiment: A tongue depressor and throat viewing assembly in accordance with the invention, as shown in FIG. 1 and 2 includes a flat blade 10 for depressing the tongue of a subject in order to fully expose his larynx so that it can be inspected by a physician and its abnormal condition then diagnosed. Blade 10 may be a conventional, commercially available disposable tongue depressor made of wood or plastic having a width and length suitable for inducing a gag reflex causing the throat to dilate to fully expose the larynx.

This reflex occurs when the blade is pressed down on the tongue or advanced to a degree causing the patient to gag or retch. The resultant throat spasm dilates the throat and in doing so fully exposes the larynx to view. This action is momentary, hence there is a limited period during which one can obtain an image of the larynx. For a proper inspection of the larynx and a diagnosis of its condition, the larynx must be viewed during its momentary reflex interval in which it is fully exposed and all aspects of its condition are revealed so the image then obtained can be recorded and preserved.

Adhered to blade, 10 adjacent its leading end is a temperature-sensitive, chromatic, discshaped sticker 11. Sticker 11 is coated with a material whose color varies as a function of temperature, the color therefore being indicative of the temperature to which the sticker is exposed. Such coatings are known, being used for example in connection with a fabric pad applied to the body to indicate in terms of color the temperature of the sign engaged by the pad.

When tongue depressor blade 10 carrying sticker 11 at its front end is inserted into the throat, the resultant color of the sicker reflects the temperature in the region of the larynx. Since a larynx disorder may be accompanied by an abnormal temperature, a proper examination of the larynx requires that the temperature or the larynx region be read.

In a system in accordance with the invention in which an image of the larynx is presented on a monitor screen in a magnified scale included in the image is an image of the sticker showing its color. To translate this color into a temperature reading, use is made of a color-to-temperature converter chart having a temperature scale (F° or C°), and a parallel color scale so that one can relate each degree of temperature to a distinctive color. This scale can be incorporated in the computer in which the video data is entered, the computer translating the color of the sticker to a temperature reading.

Attached to the trailing end of blade 10 is a light source and throat viewer unit 12, the attachment being made by means of a bracket 13. Bracket 13 has a forward section formed by parallel branches 13A and 13B adapted to receive and frictionally retain the trailing end portion of the blade, the branches engaging opposite edges of the blade.

Unit 12 which is housed in a rectangular casing 15 is mounted on the upstanding rear section 13C of the bracket so that the unit faces the forward end of the assembly. Clamped onto blade 10 at a position in front of unit 12 is a plate 14 of transparent acrylic or similar plastic material of high transparency. Plate 14 is permeable to light but acts as an impermeable barrier with respect to air borne bacteria or other contaminants emanating from the throat when the blade is inserted therein.

Barrier 14 therefore isolates unit 12 from contaminants emitted in the course of a larynx examination. This protection is necessary, for while blade 10 is disposable, unit 12 is not discarded after a single use, but may be used in future examinations, it only being then necessary to attach the unit 12 to a fresh depressor blade.

Housed in unit 12 is a miniature, high-intensity light bulb 15 socketed in a conical reflector to project a concentrated beam of light into the throat. Bulb 15 is connected by a flexible power line 16 extending from the unit to an external power source such as battery 17 shown in FIG. 3.

Also housed in unit 12 is a miniature, digital video camera 18. This camera which is focused to view the larynx, yields when the larynx is exposed and illuminated, a digital video image thereof. Miniature video cameras of this type are known, for they are now in medical use in examination procedures in which the miniature camera is introduced into an internal duct, such as the colon.

Figure 4:
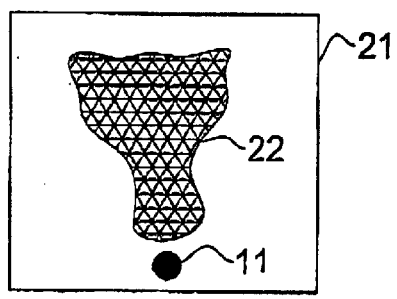
FIG. 4 illustrates an image of a larynx exhibited on the monitor screen.

As shown in FIG. 3, video digital signals yielded by miniature video camera 18 of the unit are fed via cable 19 to the input of a computer 20 having a monitor screen 21. Hence when a physician conducts a larynx examination and inserts the blade of the assembly into the mouth of the patient to depress the tongue, what he will then see on the monitor screen 21 is an enlarged image of the larynx 22, as shown in FIG. 4. Since the camera also sees sticker 11 at the front end of the blade, included in the image of the larynx is a color disc 11, whose color is indicative of the temperature in the larynx region.

Of greatest medical interest is the image of the larynx that appears when the larynx is fully exposed. This occurs in the brief interval when the tongue depressor is manipulated to induce a gag reflex or throat spasm dilating the throat. When in the examination procedure, the operator viewing an image of the larynx on screen 21 sees the effect of a gag reflex, it is at this instant that the operator, by pressing an appropriate key on a keyboard 23 associated with the computer 20, then instructs the computer to store the larynx image in a database 24.

Having captured and recorded the image of the fully exposed larynx, the physician can now diagnose the abnormal condition of his patient's larynx and prescribe a treatment for this disorder. The physician can then, by way of keyboard 23, enter into the patient's database record which includes the image of the lay, his diagnosis and prescribed treatment, and whatever other data he has obtained, from an initial examination of the patient. A hard copy of the patient's record stored in the computer can be obtained from a printer 25 associated with the computer, thereby providing the examining physician with a picture of the magnified larynx which reveals all aspects of its condition.

The record stored in the computer of the initial examination of the patient serves a highly useful function, for it can be later compared with records obtained from subsequent examinations, the differences therebetween indicating whether or not the patient's condition has improved, hence the effectiveness of the treatment. Copies of the records stored in the computer 20 can be conveyed digitally over line 26 to an Internet highway for transmission to web sites and E-mail addresses on the highway.

While there has been described a preferred embodiment of an assembly in accordance with the invention and a computer monitor station associated therewith, it is to be understood that many changes may be made therein without departing from the essential spirit of the invention.

Thus instead of including in unit 12 of the assembly a miniature video camera to obtain an image of the larynx, one can put in the unit the image input end of a fiber optics image transmission cable whose output end is coupled to a video camera, the digital output signal of this camera being fed into the computer.

To facilitate examination of the larynx, it is desirable that a gag reflex be induced by the tongue depressor to dilate the throat and more fully expose the larynx. However, in some instances, one can obtain an adequate view of the larynx by means of a tongue depressor without inducing a gag reflex.

Rather than being conveyed to an external station by a cable as shown, the signals yielded by the video camera in the unit attached to the tongue depressor blade may be conveyed to this station by wireless means, such as by a miniature microwave or infrared wave transmitter integrated with the unit. And the camera for viewing the exposed larynx need not be a video camera but may be an infrared radiation camera responsive to infrared radiation emanating from the region of the larynx to create an image thereof.

The larynx is a voice box and unvocalized sounds emanating from the larynx region may be of diagnostic significance. These sounds cannot effectively be picked up by a stethoscope, nor by placing a microphone against the throat of the subject. In order therefore to be able to hear as well as to see the larynx being examined, one may mount a miniature microphone 27 on the leading end of the tongue depressor blade 10, a fine wire link from the microphone being plugged into unit 12 so that the audio signals from the microphone can be conveyed to the monitoring station associated with the unit.

Second Embodiment: In the embodiment of an instrument in accordance with the invention shown in FIG. 1 the light source and camera unit 12 is secured by a bracket 13 to the rear end of a straight tongue depressor blade 10 which is opaque. In order to isolate the unit from contaminants issuing from the mouth of the subject being examined without interfering with the operation of the unit a transparent barrier plate 14 is mounted on the blade.

Figure 5:
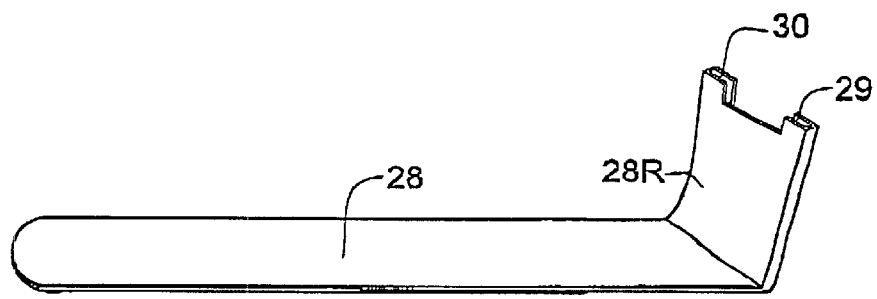
FIG. 5 is a side view of a tongue depressor and throat viewing assembly in accordance with another embodiment of the invention.
Figure 6:
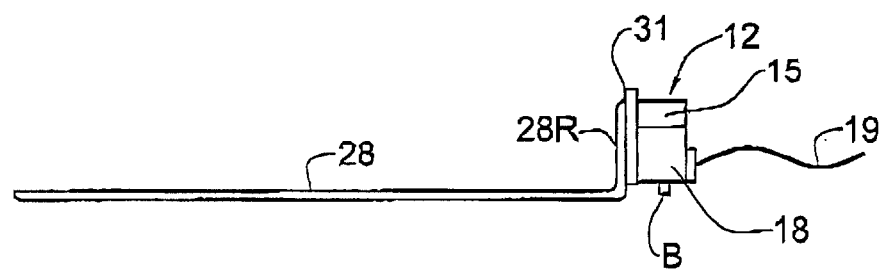
FIG. 6 is a separate view of the tongue depressor.

To avoid the need for a mounting bracket and for a barrier plate, in the embodiment of the instrument shown in FIGS. 5 and 6, there is included a tongue depressor blade 28 molded of highly-transparent synthetic plastic material such as an acrylic. Blade 28 is shaped to define an upright rear section 28R whose opposite edges are turned in to form channels 29 and 30.

The light source and video camera unit is mountable on rear section 28R of the blade and for this purpose is provided with a pair of side rails 31 which slide into channels 29 and 30 so that the unit is then placed behind the transparent upper section 28R which now acts as a contaminant barrier without however blocking the passage of light.

Blade 28 is disposable, and upon completion of an examination with the blade, the light source camera unit 12 is detached from the blade which is no longer sterile and the unit is then attached to a flesh blade for re-use.

Operating Procedures: When tongue depressor blade 10 acts to fully expose the larynx of a subject, then projected into the throat of the subject is a light beam emerging from light source 15 in unit 12 mounted on the rear end of the blade. Because, light source 15 is placed just above video camera 18, its light beam is in close proximity to the eye of the camera which therefore is able to see whatever is illuminated by the beam.

Light source 15 produces a relatively narrow beam of light rays. Since 15 therefore may be constituted by a focused and collimated high-intensity light source. Because this beam is visible to the operator handling the tongue depressor, the operator is able to see whether the beam is going toward the larynx and not elsewhere. Should this light beam be misdirected, all the operator need do is to slightly flex the flexible tongue depressor blade on whose rear end is mounted the light source included in unit 12, to a degree causing the light beam to go in a direction in which the larynx is fully illuminated. And since the eye of the camera is next to the light beam as it emerges from the light source, the camera will then clearly see the illuminated larynx.

Thus as the operator is depressing the tongue of a subject with the blade 10 of the tongue depressor, he is at the same time looking into the mouth of the subject to see whether the light beam is properly directed.

The larynx is fully exposed to the eye of the camera when a gag reflex is induced in the subject by the tongue depressor blade. For purposes of larynx examination and diagnosis, it is desirable that the instrument serve to obtain the most revealing picture that can be had of the exposed larynx during the brief gag reflex period. To this end the following options are available:

Option I: In the course of a gag reflex, the video camera trained on the larynx produces successive larynx image frames, there being millisecond intervals between these frames. In order to select from these successive frames the best picture, this being the picture taken when the larynx is exposed to a maximum degree, use may be made of an image processing module. The module is incorporated in the digital camera unit mounted on the tongue depressor blade, or is included in the computer station to which the video signals from the camera are fed. The module functions to single out the best picture of the larynx and it is this picture that is made available to the physician examining the subject.

Option II: As shown in FIG. 6, unit 12 is provided at its bottom end with a button B which when depressed switches on the video camera to render it operative to take a picture of an illuminated larynx image. In order for the doctor or other operator handling the instrument to capture an image of the larynx when fully exposed to view, the operator at the instant he induces a gag reflex, presses button B to activate the camera to take a picture of this image.

Option III: The doctor asks the subject being examined to say AH . . . , a vocalization causing dilation of the throat to expose the larynx to view. The sounds emitted by the subject are electronically processed to produce a signal activating the camera when the throat opening to the larynx is at its maximum value.

Hence when using an instrument in accordance with the invention, the operating procedure must be such as to properly direct the light beam from unit 12 at the rear of the tongue depressor so that it fully illuminates the larynx and there are no dark areas, and to take a picture of the illuminated larynx only when it is fully exposed.

While there has been shown preferred embodiments of the invention, it is to be understood that many changes may be made therein without departing from the spirit of the invention.

What is claimed is:

1. A tongue depressor and throat viewing assembly adapted to facilitate inspection of the larynx of a subject and a medical diagnosis of it s condition, said assembly comprising:
   A. a flat blade insertable into the mouth of the subject to depress his tongue so as to cause his throat to expose the larynx,
   said blade having a rear end which when the blade is inserted, then projects outwardly from the mouth, said flat blade being a disposable tongue-depressor blade; and
   B. means attachable to said rear end and for projecting a light beam to illuminate the exposed larynx and to obtain an image thereof that can be conveyed to an external site at which the image is exhibited,
   said means extending rearwardly from said rear end.

2. An assembly as set forth in claim 1, in which said means is constituted by a unit containing a light source and a miniature digital camera which yields a digital signal representing the larynx image.

3. An assembly as set forth in claim 2 in which the camera is a video camera.

4. An assembly as set forth in claim 2 in which the camera is an infra-red radiation camera.

5. An assembly as set forth in claim 2, associated with a computer monitor station in which is entered said digital signal, said station including a screen to exhibit the image of the larynx produced by the signal.

6. An assembly as set forth in claim 5, further including means to store the image produced by the signal in a database to provide a digital record of the image.

7. An assembly as set forth in claim 6, in which the computer is provided with a keyboard to enter into said database, data relating to a diagnosis of the larynx.

8. An assembly as set forth in claim 7, further including a printer associated with said computer to produce a hard copy of said record.

9. An assembly as set forth in claim 8, further including means coupling the station to an Internet highway to convey said record to web sites on the highway.

10. A tongue depressor and throat viewing assembly adapted to facilitate inspection of the larynx of a subject and a medical diagnosis of its condition, said assembly comprising:
    A. a disposable flat tongue-depressor blade insertable into the mouth of the subject to depress his tongue so as to cause his throat to expose the larynx, said blade having a rear end which when the blade is inserted, then projects outwardly from the mouth; and
    B. means attachable to said rear end and extending rearwardly therefrom for projecting a light beam to illuminate the exposed larynx and to obtain an image thereof that can be conveyed to an external site at which the image is exhibited, said means comprising a unit containing a light source and a miniature digital camera which yields a digital signal representing the larynx image;
    wherein said unit is mounted on a bracket attachable to said rear end of the blade.

11. An assembly as set forth in claim 10, in which said bracket has a front section formed by a pair of parallel branches which frictionally engage opposite edges of the blade.

12. An assembly as set forth in claim 10, further including a transparent barrier mounted in the blade in front of the unit, the barrier being permeable to light but is impermeable to bacteria and other contaminants emanating from the throat of the subject being examined.

13. A tongue depressor and throat viewing assembly adapted to facilitate inspection of the larynx of a subject and a medical diagnosis of its condition, said assembly comprising:
    A. a disposable flat tongue-depressor blade insertable into the mouth of the subject to depress his tongue so as to cause his throat to expose the larynx, said blade having a rear end which when the blade is inserted, then projects outwardly from the mouth; and
    B. means attachable to said rear end and extending rearwardly therefrom for projecting a light beam to illuminate the exposed larynx and to obtain an image thereof that can be conveyed to an external site at which the image is exhibited, said means comprising a unit containing a light source and a miniature digital camera which yields a digital signal representing the larynx image;
    wherein adhered to the blade adjacent its front end is a thermally-sensitive chromatic sticker whose color is indicative of the temperature of the larynx.

14. A tongue depressor and throat viewing assembly adapted to facilitate inspection of the larynx of a subject and a medical diagnosis of its condition, said assembly comprising:
    A. a disposable flat tongue-depressor blade insertable into the mouth of the subject to depress his tongue so as to cause his throat to expose the larynx, said blade having a rear end which when the blade is inserted, then projects outwardly from the mouth; and
    B. means attachable to said rear end and extending rearwardly therefrom for projecting a light beam to illuminate the exposed larynx and to obtain an image thereof that can be conveyed to an external site at which the image is exhibited, said means comprising a unit containing a light source and a miniature digital camera which yields a digital signal representing the larynx image;
    wherein attached to the blade adjacent its front end is a microphone to pick up sounds emanating from the region of the larynx, said microphone yielding an audio signal that is recorded.

15. A tongue depressor and throat viewing assembly comprising:

A. a blade formed of transparent plastic-material insertable in the mouth of a subject to depress the tongue so as to expose the larynx, said blade having a transparent upright rear section functioning as a contaminant barrier and as a mounting; and B. a unit removably mounted on the rear section constituted by a light source projecting a beam that illuminates the exposed larynx and a miniature digital camera yielding signals representing an illuminated image of the larynx.

16. An assembly as set forth in claim 15, in which the rear section is provided with a pair of channels at opposite edges thereof, and the unit is provided with a pair of rails that are slidable into channels.

\* \* \* \* \*